United States Patent [19]

Carr

[11] Patent Number: 4,499,753
[45] Date of Patent: Feb. 19, 1985

[54] ROTATIONAL VISCOMETER FOR HIGH-PRESSURE HIGH-TEMPERATURE FLUIDS

[75] Inventor: Kenneth R. Carr, Knoxville, Tenn.

[73] Assignee: The United States of America as represented by the United States Department of Energy, Washington, D.C.

[21] Appl. No.: 501,313

[22] Filed: Jun. 6, 1983

[51] Int. Cl.³ .............................................. G01N 11/14
[52] U.S. Cl. ........................................................ 73/59
[58] Field of Search ..................................... 73/54, 59

[56] References Cited

U.S. PATENT DOCUMENTS 3,986,388 10/1976 Stolzy ..................................... 73/59

FOREIGN PATENT DOCUMENTS 2462701 2/1981 France ..................................... 73/54
1244408 9/1971 United Kingdom ..................... 73/59
714238 2/1980 U.S.S.R. .................................. 73/54

OTHER PUBLICATIONS

"Continuous Capillary Viscometers", *Instr. Engrs. Handbook*, vol. 1, Process Meas., B. G. Liptak, Ed., Chilton, Phila. (1969), p. 632.
"Rotational Industr. Viscometers", *Instr. Engrs. Handbook*, vol. 1, Process Meas., B. G. Liptak, Ed., Chilton, Phila. (1969), p. 620.
Product Bull. TD 01-E and Test Report 3251, Magne-Drive II Ser. 2.75 Packless Rot. Mixers, Autoclave Engrs., Inc., Erie, Pa.
Sugi, N. et al., *Const. & Use of Rotating Cylinder Viscometers*. in Jap. Journ. Appl. Phys., vol. 11, No. 10, pp. 1547-1588, Oct. 1972.

*Primary Examiner*—Gerald Goldberg
*Assistant Examiner*—Joseph W. Roskos
*Attorney, Agent, or Firm*—Fred O. Lewis; Stephen D. Hamel

[57] ABSTRACT

The invention is a novel rotational viscometer which is well adapted for use with fluids at high temperatures and/or pressures. In one embodiment, the viscometer includes a substantially non-magnetic tube having a closed end and having an open end in communication with a fluid whose viscosity is to be determined. An annular drive magnet is mounted for rotation about the tube. The tube encompasses and supports a rotatable shaft assembly which carries a rotor, or bob, for insertion in the fluid. Affixed to the shaft are (a) a second magnet which is magnetically coupled to the drive magnet and (b) a third magnet. In a typical operation, the drive magnet is rotated to turn the shaft assembly while the shaft rotor is immersed in the fluid. The viscous drag on the rotor causes the shaft assembly to lag the rotation of the drive magnet by an amount which is a function of the amount of viscous drag. A first magnetic pickup generates a waveform whose phase is a function of the angular position of the drive magnet. A second magnetic pickup generates a waveform whose phase is a function of the angular position of the third magnet. An output is generated indicative of the phase difference between the two waveforms.

8 Claims, 2 Drawing Figures

ROTATIONAL VISCOMETER FOR HIGH-PRESSURE HIGH-TEMPERATURE FLUIDS

The invention is a result of a contract with the United States Department of Energy.

BACKGROUND OF THE INVENTION

This invention relates generally to rotational viscometers and more particularly to rotational viscometers designed for use with fluids at high temperatures and pressures.

The invention was developed to provide a relatively simple and inexpensive instrument for monitoring viscosity and/or viscosity changes in high-temperature, high-pressure liquid streams, such as those encountered in coal-liquefaction processes. Such streams may have temperatures on the order of 900° F. and pressures of 3,000 psi or even higher. Furthermore, the streams may be highly corrosive. Conventional rotational viscometers are not well suited for operation under such severe conditions. Conventional continuous-capillary viscometer systems have been utilized in such applications but are bulky, complex, and expensive. Various conventional viscometers are described in the following publications: *Instrument Engineers' Handbook*, Vol. 1, "Process Measurement," B. G. Liptak, Chilton, Philadelphia (1969); *Viscosity and Flow Measurement*, Van Wazer et al, Interscience Publishers (1963).

SUMMARY OF THE INVENTION

It is, therefore, an object of this invention to provide a novel viscometer.

It is another object to provide a viscometer for use with fluids at high temperatures and/or pressures.

It is another object to provide a rotational viscometer which is usable with high-pressure liquids but does not require shaft seals.

It is another object to provide viscosity-responsive apparatus which is comparatively simple and inexpensive.

Other objects and advantages will be made evident hereinafter.

The invention may be summarized as apparatus for generating an output indicative of the viscosity of a fluid. The apparatus includes a tube and a shaft having a section encompassed by the tube, the shaft being rotatably supported by the tube. The shaft carries a rotor for insertion in the aforementioned fluid. A first magnet encompasses the tube and is mounted for rotation about the same. A second magnet and a lobed ferromagnetic member are affixed to the shaft in spaced-apart relation, the second magnet being in magnetically attracting relation with the first. Means are provided for rotating the first magnet to effect rotation of the shaft. Means are provided for responding to rotation of the first magnet by generating a first electrical waveform whose phase is a function of the angular position of the first magnet. Means are also provided for responding to rotation of the lobed member by generating a second electrical waveform whose phase is a function of the angular position of the member. Means are provided for generating an output indicative of the phase relationship of the first and second waveforms.

DETAILED DESCRIPTION OF THE INVENTION

Figure 1:
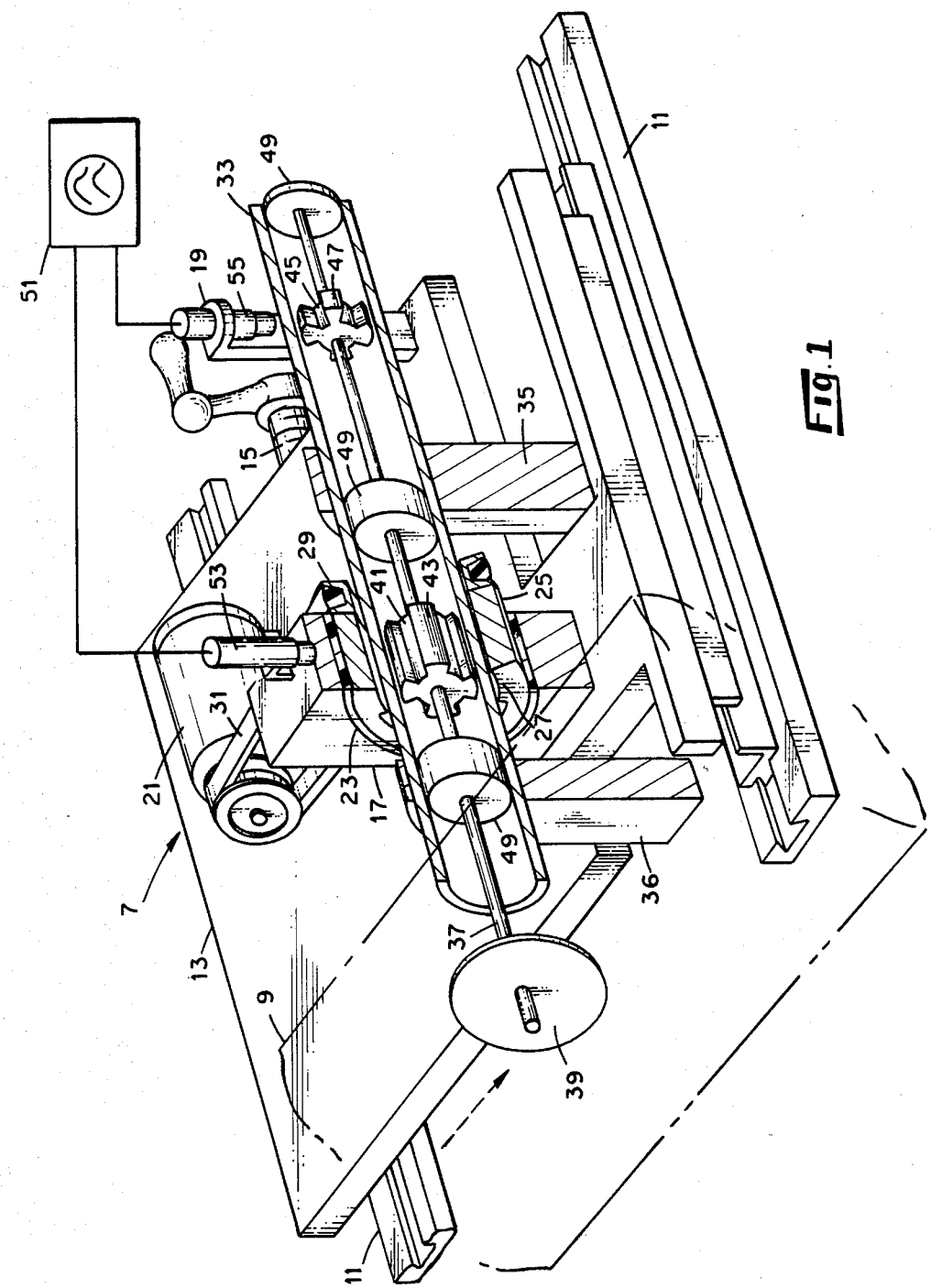
FIG. 1 is a schematic diagram of apparatus designed in accordance with the invention as used to monitor the viscosity of a liquid flowing through a pipe.

Referring to FIG. 1, the invention is illustrated in terms of apparatus 7 for measuring the viscosity of a liquid flowing through a pipe 9 (shown in phantom). The direction of liquid flow is indicated by an arrow.

The apparatus 7 includes a pair of parallel tracks 11, which are supported by any suitable base (not shown). A platform 13 is slidably fitted in the tracks for translation toward and away from the pipe 9. The platform is driven by a manually rotated shaft 15, which is supported by the aforementioned base and is threadedly engaged with the platform. Also mounted on the platform are a housing 17, a pickup-support 19, and an electric motor 21.

The housing 17 is traversed by a horizontal bore, in which a sleeve 23 is rotatably fitted. Mounted within the sleeve for rotation therewith is an annular drive magnet 25 having internal poles 27. Affixed to an end of the magnet 25 is a pulley 29, which is engaged by a belt 31 driven by the motor 21. A stationary viscometer tube 33, composed of a substantially non-magnetic material, extends freely through the drive magnet 25 and is supported by supports 35 and 36, both mounted to the base. The rearward end of the tube is closed. Its forward end is in communication with the interior of the pipe 9 and is sealably affixed thereto by any suitable means (not shown).

Coaxially disposed within the stationary tube 33 is a rotatable and axially movable shaft assembly. The assembly includes a shaft 37, whose forward end extends into the pipe 9 and terminates in a radial disk 39 (or any suitable viscometer rotor) for contacting the liquid in the pipe. Affixed to the central selection of the shaft is a magnet 41, whose external poles 43 are in attracting relation with those of the drive magnet 25. A lobed ferromagnetic member 45 is affixed to the shaft at a point relatively remote from the magnets 25, 43. In this embodiment, the member 45 is a third magnet, having pole 47. As shown, the shaft carries loose-fitting guides 49 for centering the shaft assembly in the tube 33. In addition, the magnets 25, 43 cooperatively exert a centering action on the assembly.

A conventional magnetic variable-reluctance sensor 53 is mounted to the housing 17 and is magnetically coupled with the drive magnet 25. In response to rotation of the drive magnet, the sensor generates a first sinusoidal voltage whose frequency is proportional to the speed of the drive magnet and whose phase is a function of the angular position of the drive magnet. A similar sensor 55, mounted to support 19, generates a second sinusoidal voltage which has the same frequency as the first and whose phase is a function of the angular position of magnet 45. These two voltages are fed into a standard oscilloscope 51 for displaying their phase relationship.

In a typical use of the form of the invention shown in FIG. 1, the apparatus 7 is mounted adjacent to an empty pipe through which a process liquid is to be circulated. The wall of the pipe is provided with an opening permitting insertion and removal of the viscometer disk 39, and the forward end of the viscometer tube 33 is sealed to the rim of the hole in the pipe. The platform 13 then is advanced manually toward the pipe, thus advancing the drive magnet, the shaft assembly magnetically locked therewith, the magnetic pickups, and the electric motor. The platform is advanced sufficiently to move the disk 39 to the desired measuring position within the pipe. With the process liquid flowing through the pipe under normal operating conditions, the motor 21 is energized to rotate the drive magnet 25 at a predetermined speed ensuring that the magnets 25 and 41 will rotate in synchronism. The viscous drag imposed on the rotating disk by the process fluid causes the magnet 45 to lag the drive magnet by a relatively small amount proportional to the amount of drag. Thus, the signal generated by the sensor 55 lags the signal generated by the sensor 53. The oscilloscope 51 displays these signals and the phase difference (angle) therebetween. Other things constant, the phase difference increases and decreases with the viscosity of the fluid.

To facilitate conversion of the displayed angle to viscosity, a preliminary series of viscosity measurements may be made in order to prepare a curve correlating viscosity and phase angle. Where a viscosity profile of the liquid across pipe 9 is desired, the platform 13 may be moved incrementally to make a traverse of the process stream. The range of the viscometer varies with the speed of rotation of the drive magnet 25; thus, it is convenient if the electric motor 21 is of the adjustable-speed type. In application where the liquid in pipe 9 is under pressure, the liquid will fill the tube 33. If necessary, the viscometer readout can be corrected for drag imposed on the shaft assembly by the liquid in the tube. Also, process temperature correlations may be applied to the viscosity data.

Figure 2:
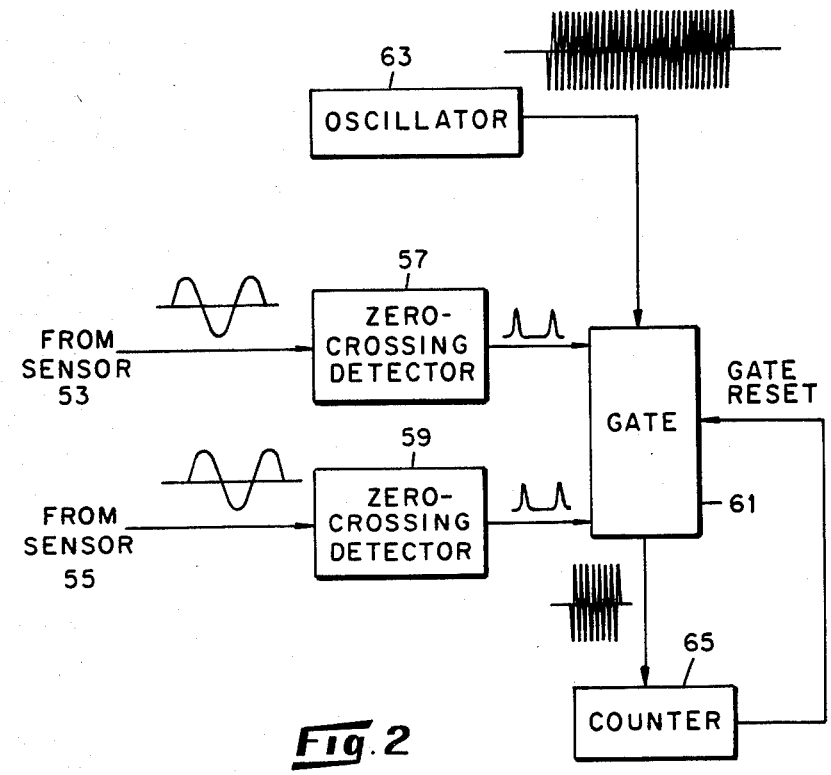
FIG. 2 is a schematic diagram of an electronic display circuit which may be incorporated in the invention.

FIG. 2 depicts a conventional electronic circuit for more precisely determining the phase difference between the signals generated by the magnetic pickups. As shown, the signals from the pickups are fed respectively to zero-crossing detectors 57 and 59, each of which generates a train of pulses with timing in accordance with its input. The two trains of pulses are fed to a gate 61, which is connected between a high-frequency oscillator 63 and a counter 65. The gate opens in response to a pulse from the detector 57 and closes in response to the next pulse from the detector 59. The number of counts registered in this interval provides a precise measurement of the phase difference between the signals from the magnetic pickups.

EXAMPLE

In a proof-of-principle experiment, a viscometer generally similar to that shown in FIG. 1 was used to display phase angles indicative of the viscosities of various static liquids contained in an open-topped vessel. The vessel was mounted on a vertically adjustable support. The apparatus 7 was positioned alongside the vessel so that the shaft 37 extended over the liquid, with the lower portion of the disk 39 immersed therein. In these experiments, the tube 33 was composed of essentially non-magnetic stainless steel; it has an outside diameter of 1⅜" and a minimum wall thickness of 0.120". The shaft 37 was composed of 316L stainless steel; its diameter was ¼" and its length was 24½". The disk was composed of aluminum and had a diameter of 6". The three magnets had four poles each and were of the Alnico type. The sensors 53 and 55 were Electro Corp. Model 3010 AN magnetic sensors. Prior to operation, torque was applied to the shaft assembly with a wrench to determine the maximum angle through which the magnet 43 could be turned relative to the drive magnet 25 before phase-lock between these magnets was lost; the maximum angle was about fifty mechanical degrees. Experiments were conducted with various liquids (e.g., water, SAE 90 motor oil, and glycerine); with various areas of the disk 39 immersed; and with the motor 21 operating at various speeds (e.g., at a speed corresponding to 42 rpm for the drive magnet 25). These tests established that the phase displacement displayed on the oscilloscope increased and decreased with the amount of drag exerted on the disk 39 by the liquid. That is, the phase angle displayed on the oscilloscope was a function of viscosity.

It will be apparent that a viscometer designed in accordance with the invention has advantages over the prior art. For instance, it is comparatively simple, compact, inexpensive, rugged, and usable at high temperatures and pressures. A significant advantage is that the viscometer does not require seals for isolating the shaft assembly from the process fluid.

The foregoing description of a preferred embodiment of the invention has been presented to best explain the principles of the invention and to enable others skilled in the art to utilize the invention in various embodiments and with various modifications suited to a particular application. It will be apparent to those versed in the art that many modifications and variations may be made in light of the foregoing teachings. For instance, in some applications the shaft assembly and drive magnet need not be made reciprocatable. In some applications the centering guides 49 may be eliminated. If desired, the lobed ferromagnetic member 45 may be an unmagnetized body which is magnetically coupled with any suitable external means for generating an electrical signal which is a function of the angular position of the rotated member. As a further example, the circuit for determining the phase difference between the signals from the magnetic sensors may be a conventional arrangement including a pair of comparators for converting the signals to square waves. The square waves are fed to an exclusive OR gate. The output from the gate is fed to an RC filter for providing a d.c. voltage whose level is proportional to the phse difference between the original signals.

It is intended that the invention be defined by the appended claims.

What is claimed is:

1. Apparatus for generating an output indicative of the viscosity of a fluid comprising:
   a tube;
   a rotatable shaft having a section thereof encompassed and supported by said tube;
   a rotor affixed to said shaft, for contacting said fluid;
   a first magnet encompassing said tube and mounted for rotation about and reciprocation along the same;
   a second magnet affixed to said shaft in magnetically attracting relation with the first magnet;
   a lobed ferromagnetic member affixed to said shaft in spaced apart relation with the second magnet;
   means for rotating the first magnet to effect rotation of said shaft;
   means for responding to rotation of the first magnet by generating a first electrical waveform whose phase is a function of the angular position of the first magnet;

means for responding to rotation of said member by generating a second electrical waveform whose phase is a function of the angular position of said member; and means for generating an output indicative of the phase relationship of the first and second waveforms.

2. The apparatus of claim 1 wherein said tube is substantially non-magnetic.

3. The apparatus of claim 1 wherein said lobed member is a magnet.

4. The apparatus of claim 1 further characterized by said rotatable shaft being mounted for reciprocation in said tube.

5. In combination:

a vessel containing a fluid; and apparatus for generating an output indicative of the viscosity of said fluid, said apparatus comprising:

a tube having a closed end and having an open end in communication with the interior of said vessel;

a first magnet mounted for rotation about and reciprocating along said tube;

a shaft having a section thereof encompassed by and rotatably and slidably supported by said tube;

a rotor carried by said shaft and in contact with said fluid;

a second magnet affixed to said shaft, the second magnet being in attracting relation with the first magnet;

a lobed ferromagnetic member affixed to said shaft;

means for rotating the first magnet to effect rotation of said shaft;

means for responding to rotation of the first magnet by generating a first electrical waveform whose phase is a function of the angular position of the first magnet;

means for responding to rotation of said member by generating a second electrical waveform whose phase is a function of the angular position of said member; and means for generating an output indicative of the phase relationship of the first and second waveforms.

6. The combination of claim 5 wherein said tube is substantially non-magnetic.

7. The combination of claim 5 wherein said member is unmagnetized.

8. The combination of claim 5 wherein said means for respectively responding to rotation of the first magnet and said member are magnetic sensors.

* * * * *